(12) United States Patent
Wallace et al.

(10) Patent No.: US 8,163,257 B2
(45) Date of Patent: Apr. 24, 2012

(54) FLUID DISPENSER

(75) Inventors: Mark Andrew Wallace, South Staffordshire (GB); Hugh Christopher Bramley, Chipping Norton (GB); Mark John Jervis, OffChurch (GB)

(73) Assignee: IMI Vision Limited, Warwickshire (GB)

( * ) Notice: Subject to any disclaimer, the term of this patent is extended or adjusted under 35 U.S.C. 154(b) by 419 days.

(21) Appl. No.: 12/296,953

(22) PCT Filed: Apr. 13, 2007

(86) PCT No.: PCT/GB2007/001376
§ 371 (c)(1),
(2), (4) Date: Sep. 8, 2009

(87) PCT Pub. No.: WO2007/122387
PCT Pub. Date: Nov. 1, 2007

(65) Prior Publication Data
US 2010/0015009 A1 Jan. 21, 2010

(30) Foreign Application Priority Data
Apr. 13, 2006 (GB) .................................. 0607427.2

(51) Int. Cl.
*B01L 3/00* (2006.01)
(52) U.S. Cl. ......... 422/559; 422/501; 422/515; 422/522

(58) Field of Classification Search .................. 422/501, 422/509, 515, 521–522, 547, 559; 73/864.01–864.25
See application file for complete search history.

(56) References Cited

U.S. PATENT DOCUMENTS

| 4,562,871 A | | 1/1986 | Astle |
| 5,645,114 A | * | 7/1997 | Bogen et al. .................. 141/145 |
| 5,871,699 A | * | 2/1999 | Ruggeri ........................ 422/512 |
| 6,599,755 B1 | * | 7/2003 | Eipel et al. ...................... 506/40 |
| 6,698,470 B1 | * | 3/2004 | Horn et al. ..................... 141/130 |
| 2003/0141470 A1 | | 7/2003 | Igarashi |
| 2005/0186114 A1 | * | 8/2005 | Reinhardt et al. .............. 422/65 |
| 2006/0147313 A1 | * | 7/2006 | Zengerle et al. ................ 417/53 |

FOREIGN PATENT DOCUMENTS
WO WO-2005/016534 2/2005
* cited by examiner

*Primary Examiner* — Jan Ludlow
(74) *Attorney, Agent, or Firm* — The Ollila Law Group LLC

(57) ABSTRACT

A cartridge (10) for dispensing a reagent contained in a reagent reservoir (32). The reservoir (32) is in fluid communication with a deformable dispense tube (26) that is a least partially compressible, in use, to dispense a volume of reagent from the tube (26). The reservoir (32) defines an enclosed gas space (46) above the reagent, and the cartridge (10) includes a gas vent (40) that, in use, admits gas to the gas space (46) in response to dispense of reagent from the tube (26) that serves to control the reservoir pressure as the reservoir (32) is depleted by subsequent dispensing of reagent. A dispenser employing the cartridge (10) and a method of dispensing a volume of reagent are also disclosed.

12 Claims, 11 Drawing Sheets

FLUID DISPENSER

CROSS-REFERENCE TO RELATED APPLICATIONS

This is a National Stage entry of International Application No. PCT/GB2007/001376, with an international filing date of Apr. 13, 2007, which claims priority of Great Britain patent application no. 0607427.2, filed Apr. 13, 2006, entitled "Fluid Dispenser".

This invention relates to the dispensing of fluid and in particular, but not exclusively, to a device for accurately micro-dosing a small volume of fluid, for example an in-vitro diagnostic (IVD) test reagent.

During diagnosis or observation of patients, it is common to take a biological sample in order to conduct IVD tests. The biological sample is typically taken in the form of a blood, urine or stool sample.

The sample is then forwarded to an IVD laboratory which performs the IVD tests in bulk.

Samples may be prepared prior to diagnostics tests being carried out. Commonly, specific components of the samples are isolated, for example serum may be separated from blood.

In order to provide for economies, the IVD laboratories typically operate a number of large automated IVD test machines which perform IVD tests in volume on a production line basis.

The performing of IVD tests may be automated as follows. A prepared biological sample is added to a cuvette or other vessel mounted on a carousel on the IVD machine. The particular reagent required for the given IVD test is brought on station from a second carousel containing a number of different reagents. Whilst on station, the reagent container is opened, and a pipette inserted into the reagent in order to withdraw a volume of fluid. The pipette is then moved by the machine into a position directly above the cuvette and the required volume of reagent is typically dispensed into the cuvette by a positive displacement pump, for example, a syringe driven by a stepper motor. Following the dispensing of the reagent, the pipette is then moved off station, and the pipette tip is washed and rinsed, or alternatively discarded in the case of a disposable pipette.

This dispensing process is complex and expensive, particularly where the pipette is washed and rinsed following each and every dispense of reagent. Furthermore, the machine is required to move the pipette from the reagent container to the cuvette and then to a further position at which the pipette is washed. This movement adds to the complexity of the machine, leading to an increased risk of component failure. Additionally, the movement of the machine leads to a long cycle time for each reagent dispense. This in turn limits the throughput of the machine, and thereby the speed with which the laboratory can return the test results to the health care professionals.

A known solution to this problem is to provide a cartridge which contains both a reservoir of reagent and a multi-use dispense tube. This solution is advantageous in that the dispense tube does not need to be washed or discarded after each and every dispense. Also, the movement of the machine is limited to the delivery of the required cartridge to a dispense station. As soon as the delivery of reagent is completed, the next reagent cartridge can be brought into position. The dispense tube used in this particular solution is of the type disclosed in patent number WO 2005/016534 which describes a flexible dispense tube which is struck by a hammer in order to dispense a known volume of fluid from the tube. Since the tube has a very small internal diameter, the volume of fluid dispensed by a single strike of the tube is in the order of 100 nanoliters.

However, a typical volume of reagent to be dispensed in IVD testing is in the region of 1 to 100 microliters. Given that each cartridge is required to dispense up to 1000 reagent doses, the reservoir volume is in the region of 1 to 100 milliliters. It is therefore possible that the change in reservoir volume will be as much as 100 milliliters from full to empty. Such a change in volume will inevitably lead to a substantial change in liquid head pressure between the condition when the reservoir is full and the condition when the reservoir is approaching empty.

However, the dispense tube of WO 2005/016534 is designed to dispense volumes in the region of 100 nanoliters and consequently is not configured to operate under changing reservoir pressure conditions since the change in liquid volume before and after the reagent shot is minimal.

Consequently, the dispense tube technology of WO 2005/016534 is not at present suited to operating under variable head pressure conditions, which presents a substantial impairment to the performance of the dispense tube in the field of reagent dispensing.

Additionally, the dispense tube is not readily sealable to prevent leakage during transit of the device. Furthermore, the dispense tube requires priming before the first reagent shot since the tube will not dispense liquid, or draw liquid into the dispense tube, when the dispense tube does not already contain a volume of reagent.

For the avoidance of doubt, the term 'head pressure' refers to the liquid head pressure of the reagent. The term 'reservoir pressure' refers to the total pressure observed at the base of the reservoir.

It is an object of the current invention to provide a device for dispensing IVD reagent which at least mitigates some of the above problems, and in particular, provides a device which will at least control the reservoir pressure as the reservoir is depleted during normal operation.

According to a first aspect of the present invention there is provided a reagent dispense device comprising, a reagent reservoir in fluid communication with a deformable dispense tube, the deformable dispense tube being at least partially compressible, in use, between a hammer and an anvil, so as to dispense a volume of reagent from the tube, wherein, in use, the reservoir defines an enclosed gas space above the reagent, and the device including a gas vent for, in use, admitting gas to the gas space in response to a dispense of reagent from the tube, the passage of gas into the gas space serving to control the reservoir pressure as the reservoir is depleted by subsequent dispensing of reagent.

Since the volume of reagent dispensed from the dispensing tube is highly dependent upon the reservoir pressure, it is desired that the reservoir pressure is maintained as close to a constant level as is practicable. The current invention achieves what approximates to a constant reservoir pressure by admitting a volume of gas into the enclosed gas space, thereby compensating the reduction in head pressure with an increase in the pressure in the gas space above the reagent. Additionally the head pressure in the tube is balanced by the surface tension forces at the tube outlet and vent outlet. This in turn allows increased flow rate which is a further advantage of the invention.

Preferably, the vent outlet is arranged at the base of the reservoir. This is advantageous in that the reservoir pressure in the reagent reservoir can only be kept constant when there is an enclosed gas space above the reagent. As soon as the level of the reagent drops below the vent, the sub-atmospheric pressure generated in the gas space above the reagent is relieved by the free introduction into the gas space of gas via the vent. By placing the vent as low as possible in the reservoir, the volume of reagent which may be dispensed at constant head pressure is therefore increased.

Preferably, the vent has an inlet arranged at a top surface of the reservoir.

Such an arrangement provides advantages in terms of the method of manufacture of the device since the reservoir can be formed from a two-part moulding.

Preferably, the vent is in the form of a tube.

Preferably, the outlet of the tube has a saw tooth configuration in order to minimise surface tension effects at the outlet which may impair the formation of bubbles.

Preferably, the reservoir defines multiple chambers which are successively drained of reagent so as to minimise the effective gas space above the reagent.

It has been found that the reservoir pressure fluctuates due to the generation of bubbles at the vent outlet and their subsequent displacement through the reagent and into the gas space. In particular, it has been discovered that the reservoir pressure increases at the moment that the bubble is formed at the vent outlet. It has also been discovered that the size of the bubble generated at the vent outlet varies with the volume of the gas space, in this case air space, above the reagent, specifically, the larger the gas volume above the reagent, the larger the bubble generated at the vent outlet. Since the fluctuation in pressure is proportional to the size of the bubble generated at the vent outlet, it has been found advantageous to minimise the volume of gas space above the reagent. The current invention, in a preferred embodiment, achieves this reduction in volume (for the same volume of reagent) by compartmentalising the reservoir. Each compartment is drained of reagent successively, the gas venting into one compartment until it is emptied, thereby providing access to vent into the next compartment, and so on. The effective gas space is therefore dictated by the number of compartments provided in the reservoir. The provision of compartments therefore reduces the fluctuation in head pressure by reducing the bubble size and consequently improves the performance of the dispensing tube.

Preferably, the compartments are separated by a series of upstanding walls which extend from an upper wall of the reservoir to a position approximate to a lower wall in the reservoir.

Preferably, a conduit is formed between the compartments, the conduit being arranged approximately at the reservoir base.

Preferably, the chambers are drained successively, the vent outlet being provided in a first chamber and a fluid conduit connecting the reservoir to the deformable dispense tube being arranged in the last chamber.

Preferably, the device includes a shroud which partially surrounds the dispense tube so as to protect the tube from damage.

Preferably, the shroud has a portion adjacent to, but not touching the tube outlet.

Preferably, the shroud defines an aperture shaped to co-operate with the anvil in order to allow the anvil access to the tube in order to dispense the reagent.

Preferably, the volume of reagent dispensed from the dispense tube for each strike of a hammer is one hundred (100) nanoliters.

Preferably, the device is provided with a radio frequency identification (RFID) chip containing data such as reagent type, shelf life, date of manufacture, remaining reagent volume, and other such information as may be required.

According to a second aspect of the invention there is provided an apparatus for dispensing a volume of reagent from the dispense device of the first aspect of the invention, the apparatus comprising a hammer and a co-operating anvil, both mounted in a housing suitable for receiving the dispense device, the hammer, in use, being arranged to strike the dispense tube, thereby at least partially compressing the tube against the anvil so as to dispense a volume of reagent from the tube, wherein the hammer is displaced by a first linear actuator mounted at a fixed position in the housing, and the anvil is moveable by a second linear actuator so as to calibrate the position of the anvil relative to the hammer.

The dispensing apparatus of the present invention thereby allows for the rapid mounting of the dispense device on the dispensing apparatus and the rapid calibration of the dispensing apparatus prior to the dispensing of the reagent. This greatly reduces the complexity of the machine operations to be performed by a reagent dispensing machine in which the apparatus is used.

Preferably, the housing is defined by a hammer body and an anvil body.

Preferably, the position of an inner face of the hammer body is matched to an actuated position of the hammer.

Preferably, the inner face of the hammer body is configured to receive the shroud, thereby calibrating the hammer actuated position to the position of the tube.

Preferably, the operation position of the anvil is matched to the actuated position of the hammer.

Preferably, the first linear actuator is a Piezo stack.

Preferably, the second linear actuator is a stepper motor with a lead screw, to give a linear output.

According to a third aspect of the current invention there is provided a method of dispensing a volume of fluid, including the steps of:

providing a dispensing apparatus according to the previous aspect of the invention, and a controller for controlling the dispense apparatus, inserting the dispense device into the housing, driving the hammer to its actuated position to align the hammer against the tube, then driving the anvil towards the hammer until the controller detects contact therebetween, then retracting the anvil a pre-determined distance so as to calibrate the position of the anvil to the actuated position of the hammer, then actuating the hammer to strike the tube so as to dispense a volume of fluid.

Preferably, the method includes the additional steps of retracting the hammer from the tube.

Preferably, the method includes the further additional step of cycling the hammer to repeatedly dispense a series of discreet volumes of reagent from the tube.

According to a fourth aspect of the present invention there is provided a liquid dispense device comprising, a liquid reservoir in fluid communication with a deformable dispense tube, the deformable dispense tube being at least partially compressible, in use, between a hammer and an anvil, so as to dispense a volume of liquid from the tube, wherein, in use, the reservoir defines an enclosed gas space above the liquid, and the device including a gas vent for, in use, admitting gas to the gas space in response to a dispense of liquid from the tube, the passage of gas into the gas space serving to control the reservoir pressure as the reservoir is depleted by subsequent dispensing of liquid.

Preferably, the vent outlet is arranged at the base of the reservoir.

Preferably, the vent has an inlet arranged at a top surface of the reservoir.

Preferably, the vent is in the form of a tube.

Preferably, the outlet of the tube has a saw tooth configuration in order to minimise surface tension effects at the outlet which may impair the formation of bubbles.

Preferably, the reservoir defines multiple chambers which are successively drained of liquid so as to minimise the effective gas space above the liquid.

Preferably, the compartments are separated by a series of upstanding walls which extend from an upper wall of the reservoir to a position approximate to a lower wall in the reservoir.

Preferably, a conduit is formed between the compartments, the conduit being arranged approximately at the reservoir base.

Preferably, the chambers are drained successively, the vent outlet being provided in a first chamber and a fluid conduit connecting the reservoir to the deformable dispense tube being arranged in the last chamber.

Preferably, the device includes a shroud which partially surrounds the dispense tube so as to protect the tube from damage.

Preferably, the shroud has a portion adjacent to, but not touching the tube outlet.

Preferably, the shroud defines an aperture shaped to co-operate with the anvil in order to allow the anvil access to the tube in order to dispense the liquid.

Preferably, the volume of liquid dispensed from the dispense tube for each strike of a hammer is one hundred (100) nanoliters.

Preferably, the device is provided with a radio frequency identification (RFID) chip containing data such as liquid type, shelf life, date of manufacture, remaining liquid volume, and other such information as may be required.

According to a fifth aspect of the invention there is provided an apparatus for dispensing a volume of liquid from the dispense device of the fourth aspect of the invention, the apparatus comprising a hammer and a co-operating anvil, both mounted in a housing suitable for receiving the dispense device, the hammer, in use, being arranged to strike the dispense tube, thereby at least partially compressing the tube against the anvil so as to dispense a volume of liquid from the tube, wherein the hammer is displaced by a first linear actuator mounted at a fixed position in the housing, and the anvil is moveable by a second linear actuator so as to calibrate the position of the anvil relative to the hammer.

Preferably, the housing is defined by a hammer body and an anvil body.

Preferably, the position of an inner face of the hammer body is matched to an actuated position of the hammer.

Preferably, the inner face of the hammer body is configured to receive the shroud, thereby calibrating the hammer actuated position to the position of the tube.

Preferably, the operation position of the anvil is matched to the actuated position of the hammer.

Preferably, the first linear actuator is a Piezo stack.

Preferably, the second linear actuator is a stepper motor with a lead screw, to give a linear output.

According to a sixth aspect of the current invention there is provided a method of dispensing a volume of fluid, including the steps of:

providing a dispensing apparatus according to the previous aspect of the invention, and a controller for controlling the dispense apparatus, inserting the dispense device into the housing, driving the hammer to its actuated position to align the hammer against the tube, then driving the anvil towards the hammer until the controller detects contact therebetween, then retracting the anvil a pre-determined distance so as to calibrate the position of the anvil to the actuated position of the hammer, then actuating the hammer to strike the tube so as to dispense a volume of fluid.

Preferably, the method includes the additional steps of retracting the hammer from the tube.

Preferably, the method includes the further additional step of cycling the hammer to repeatedly dispense a series of discreet volumes of liquid from the tube.

The invention will now be described by way of example only, and will reference to the following drawings, in which.

Figure 1:
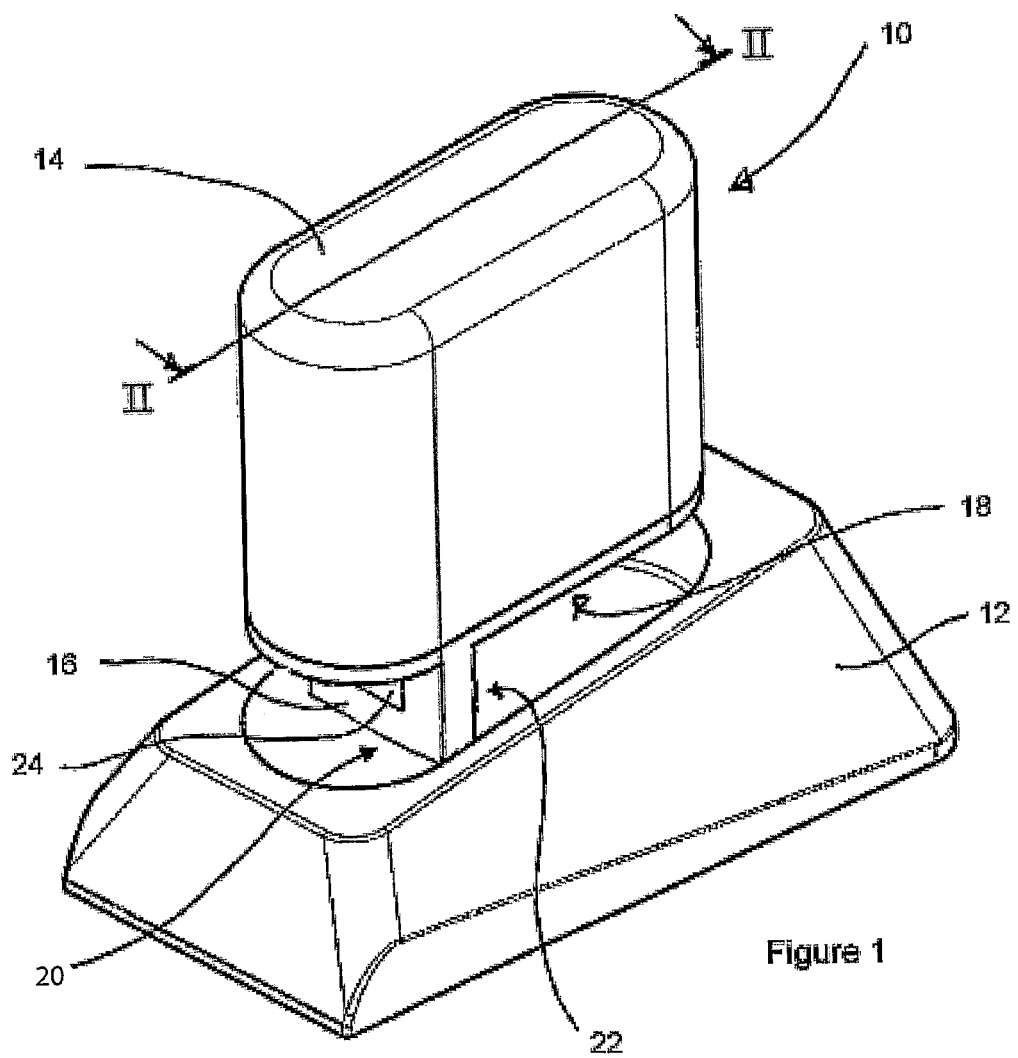
FIG. 1 is an isometric view of the reagent dispense device according to the present invention, showing the device mounted in a docking station.
Figure 8:
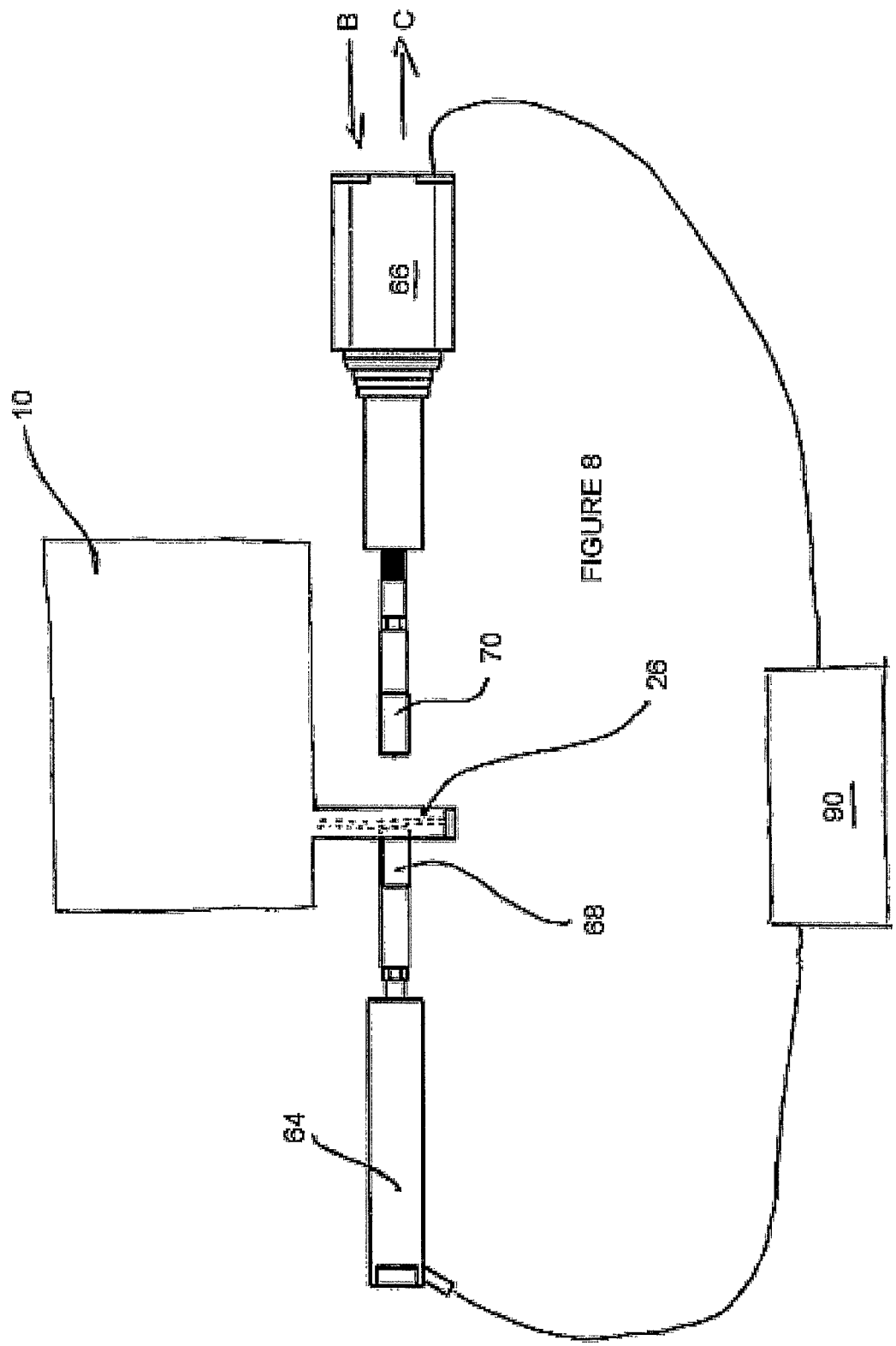
FIG. 8 is a side view of the reagent dispensing apparatus and the shroud as shown in FIGS. 6 and 7.
Figure 9:
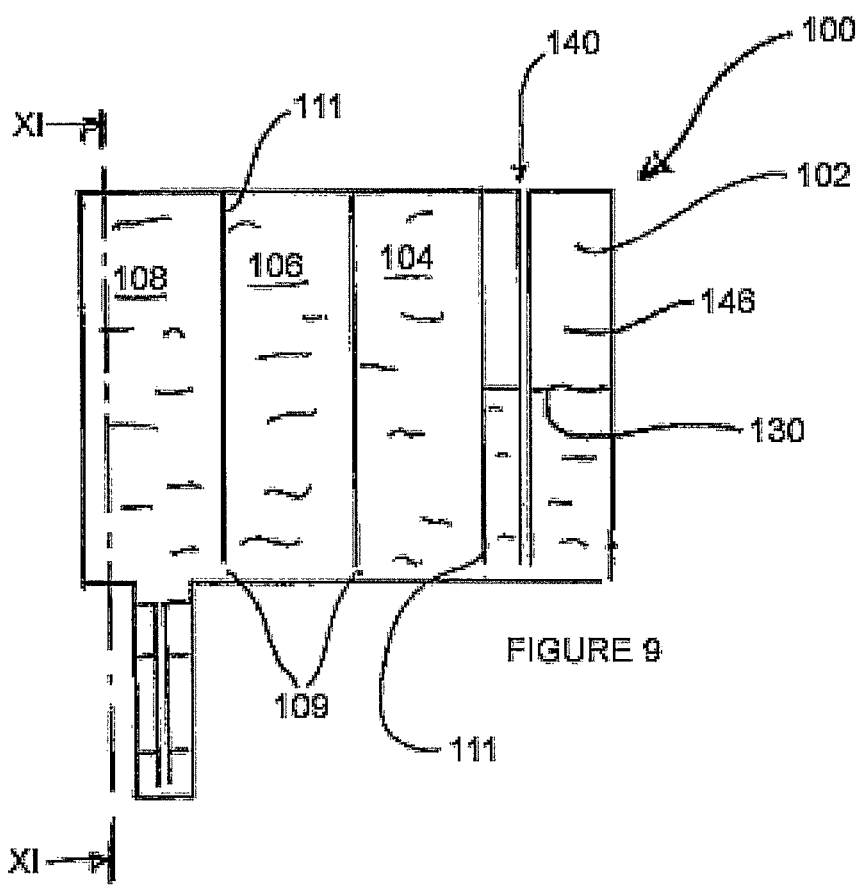
FIG. 9 is a sectioned side view of a further alternative embodiment of reagent dispense device according to the present invention sectioned along line IX-IX in FIG. 11 and showing the first chamber part-full.
Figure 11:
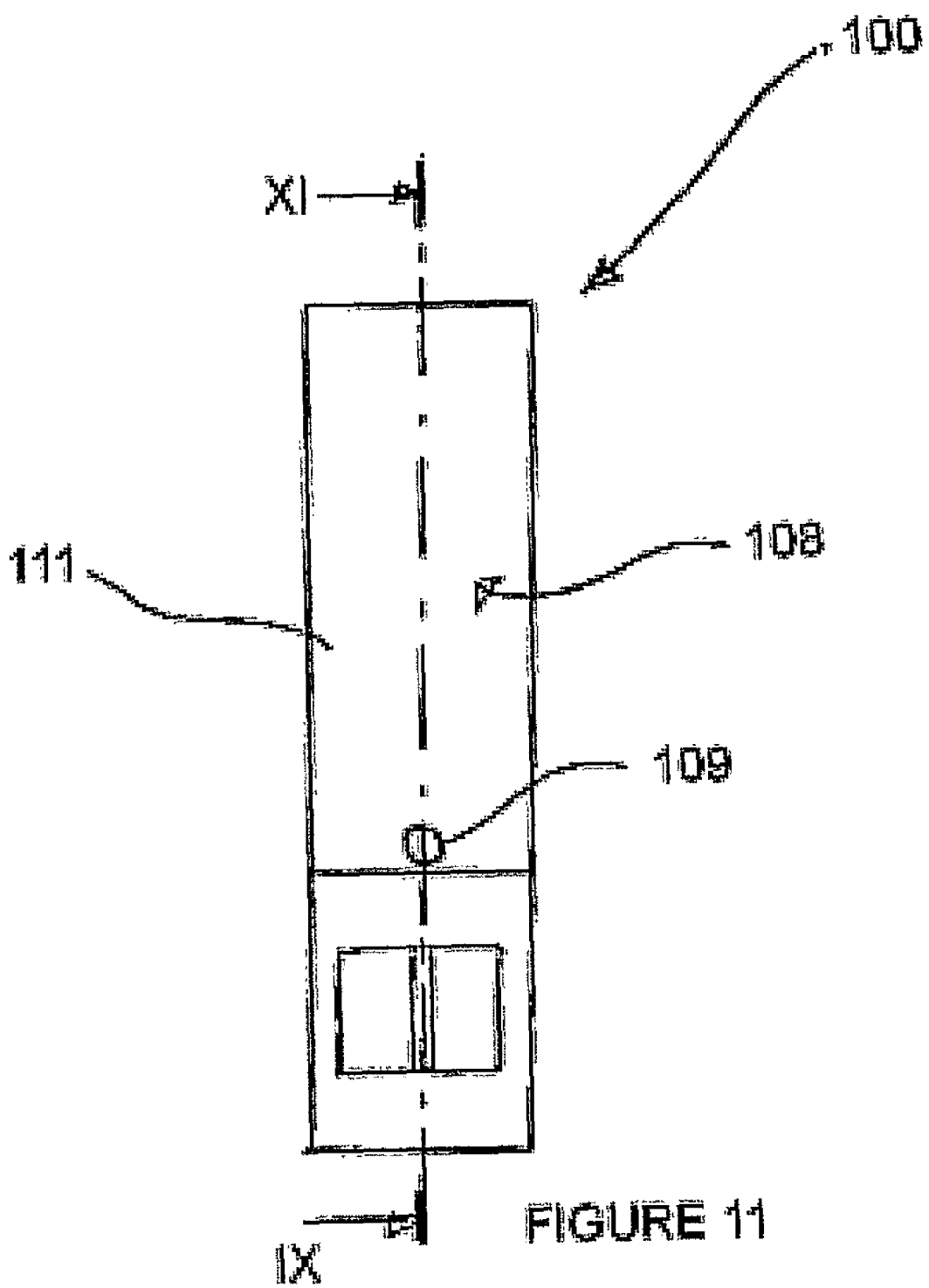
Figure 12:
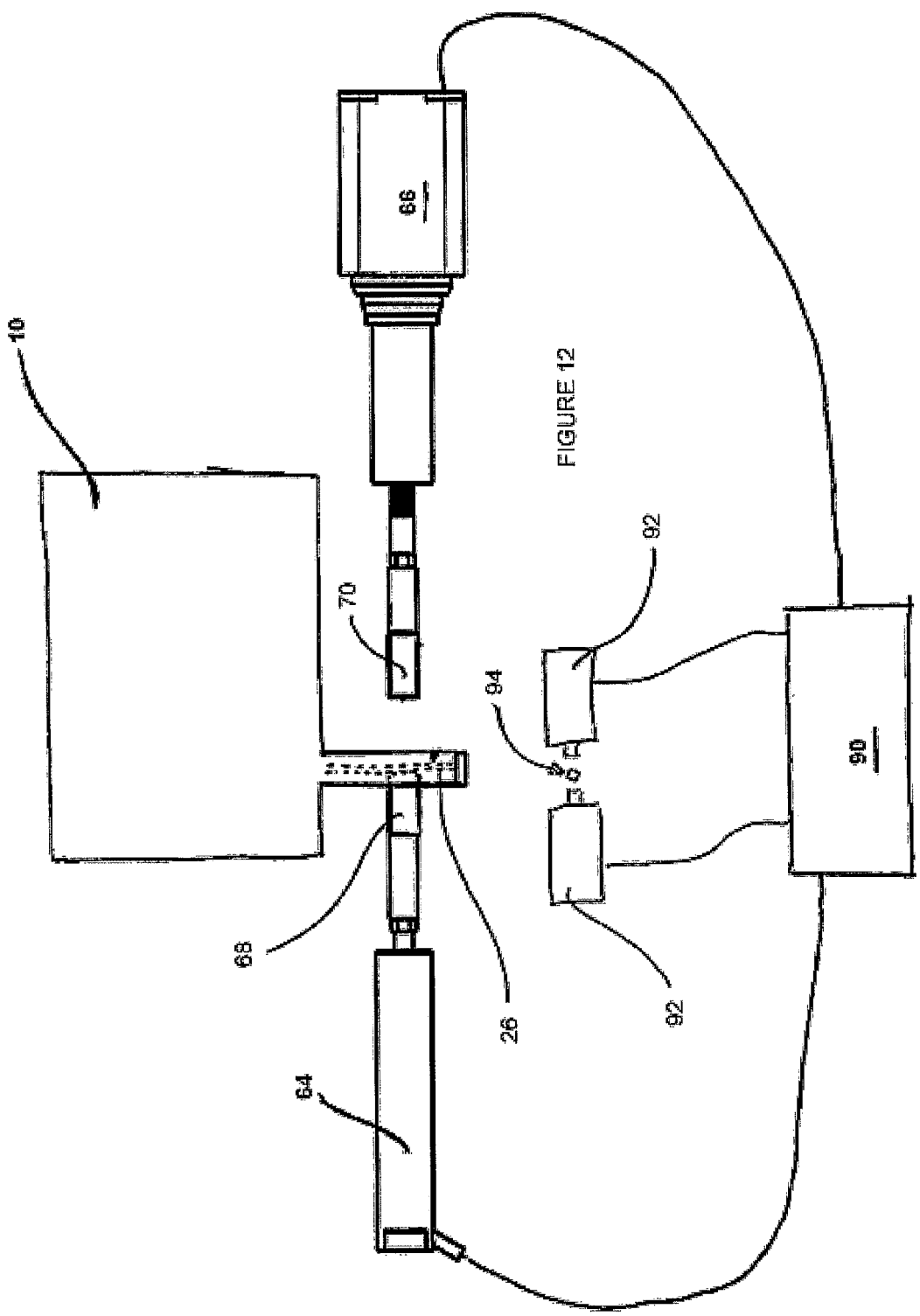
Figure 13:
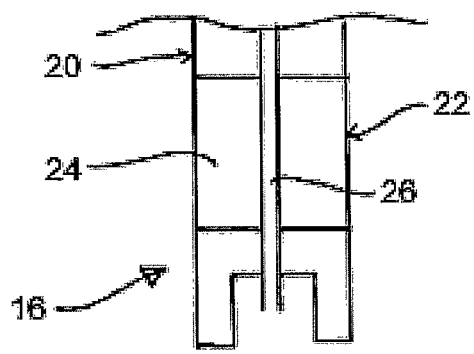
Figure 14:
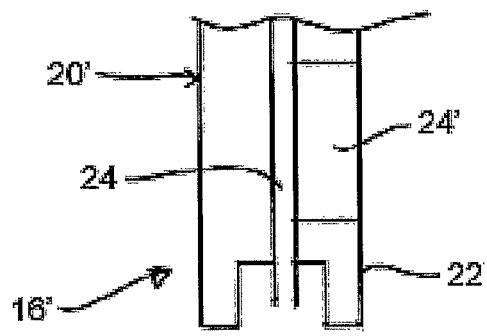
Figure 15:
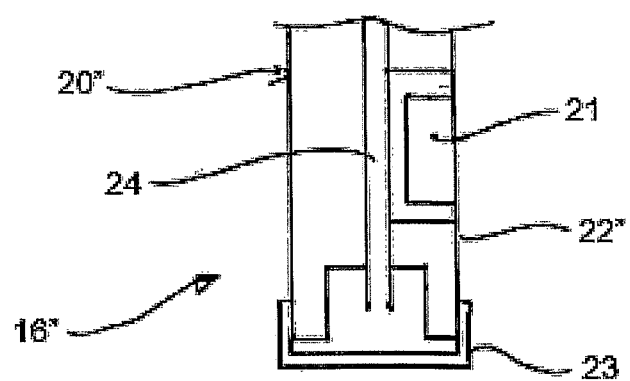

FIG. 11 is an end view of the reagent dispense device of FIG. 9 sectioned along line XI-XI in FIG. 9, FIG. 12 is a side view of the reagent dispensing apparatus of FIG. 8 including a droplet size measurement device, FIG. 13 is a partial side view of the shroud portion of the reagent dispense device of FIG. 1 sectioned along the line II-II as shown in FIG. 1, FIG. 14 is a partial side view of an alternative embodiment of shroud portion to that shown in FIG. 13, and FIG. 15 is a partial side view of a yet further alternative embodiment of shroud portion to that shown in FIGS. 13 and 14.

Figure 2:
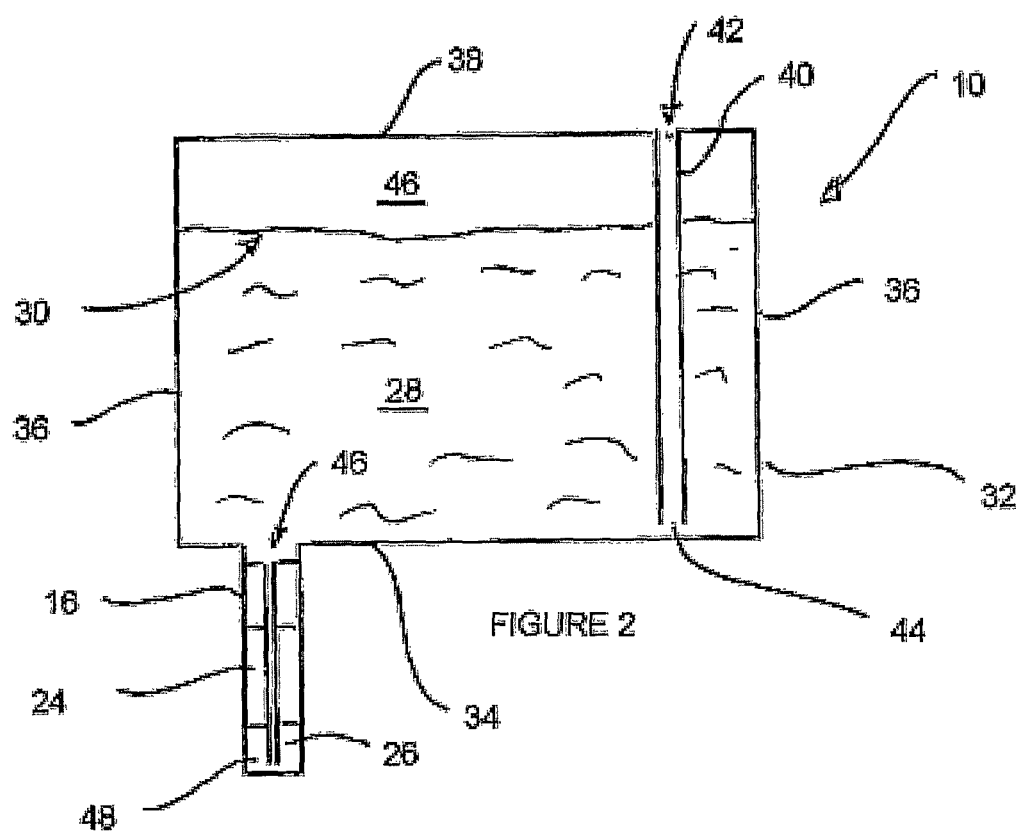
FIG. 2 is a side view of the reagent dispense device sectioned along the line II-II as shown in FIG. 1.

In FIG. 1 a liquid, in this instance, reagent dispense device, in the form of a cartridge 10 is shown mounted in a docking station 12. The reagent dispense cartridge 10 has a cartridge body 14 and a shroud portion 16. The shroud portion extends downwardly from a lower surface 18 of the cartridge body 14. The shroud portion 16 has a front face 20 and a rear face 22. Extending between the front and rear faces 20, 22 is an aperture 24. The shroud portion 16 carries a dispensing tube 26 which passes substantially vertically (as shown in FIG. 2) through the aperture 24. An upper end of the dispensing tube rests within the cartridge body 14 as will be described in further detail shortly. The shroud portion is shown in greater detail in FIG. 13.

Referring now to FIG. 2, the reagent cartridge 10 is shown containing a volume of reagent 28 which defines a reagent level 30. The reagent 28 is contained within a reagent reservoir indicated generally at 32. The reservoir defines a reservoir base 34, side walls 36 and a reservoir upper wall 38. The reservoir 32 also comprises a vent 40 which has an inlet 42 and an outlet 44. In transit and storage the inlet 42 can be optionally covered with a break-off tab so as to seal the reservoir from atmosphere. This has the added advantage of preventing leaking from the cartridge as no gas can enter the reservoir. The outlet 44 is arranged proximate the reservoir base 34 and has a saw tooth profile in order to encourage the separation of bubbles from the vent 40. Alternatively the outlet of the vent 40 may be angled to the elongate axis of the tube in order to produce an elliptical outlet which further promotes separation of the bubble from the vent 40.

In use the cartridge 10 is filled through the vent inlet 42, with the cartridge arranged with the inlet 42 facing upward whilst a vacuum is applied to the reservoir outlet. Alternatively, the reagent could be pumped in through the vent inlet 42. In addition, the design of the pipe 24 is such that priming of the cartridge is achieved by capillary action.

The dispensing tube 26 is shown in fluid communication with the reagent reservoir 32 by way of a dispensing tube inlet 47. A reagent tube outlet 48 is arranged adjacent to, but slightly spaced from the bottom of the shroud portion 16.

Between the reservoir upper wall 38 and the reagent level 30 is a gas space 46, in this case filled with air. This gas space could equally well be filled with a different gas, in particular an inert gas such as argon. The purpose of this gas space will be described in further detail shortly.

Figure 3:
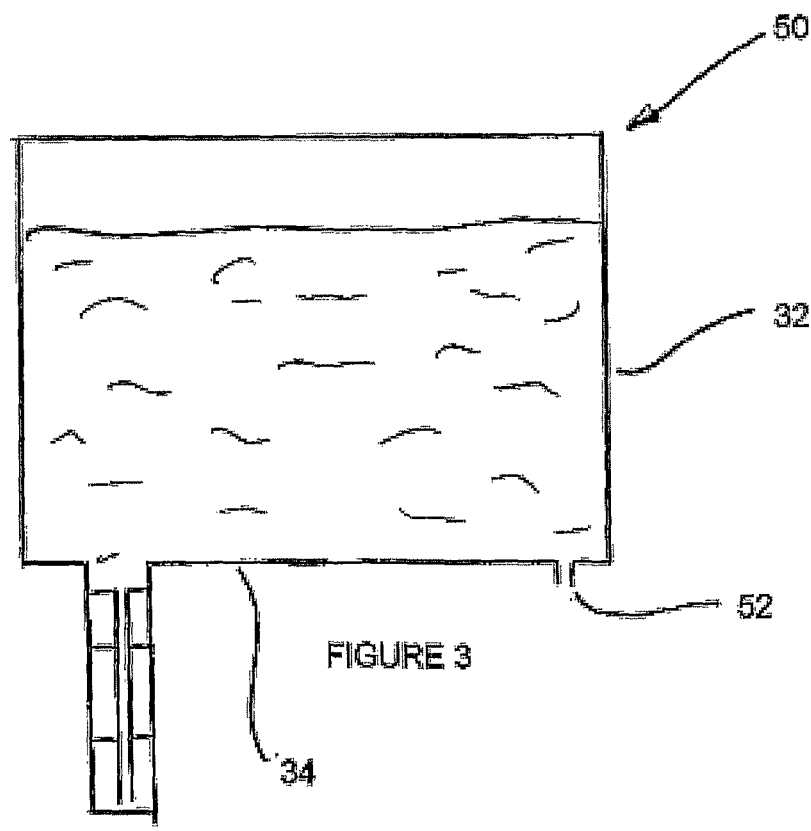
FIG. 3 is a sectioned side view of an alternative embodiment of dispense device according to the present invention.

Turning now to FIG. 3, an alternative embodiment of reagent cartridge 10 is indicated generally at 50. The cartridge 50 differs from the cartridge 10 only in that the vent 52 is provided in the base 34 of the reservoir 32 rather than taking the form of a tube which extends from the reservoir upper wall to a position proximate the reservoir base. It will be appreciated that within the scope of the invention, alternative forms of cartridge could be provided having a different shape to the cartridges 10, 50 and with vents provided at alternative locations to those of cartridges 10 and 50.

Figure 4:
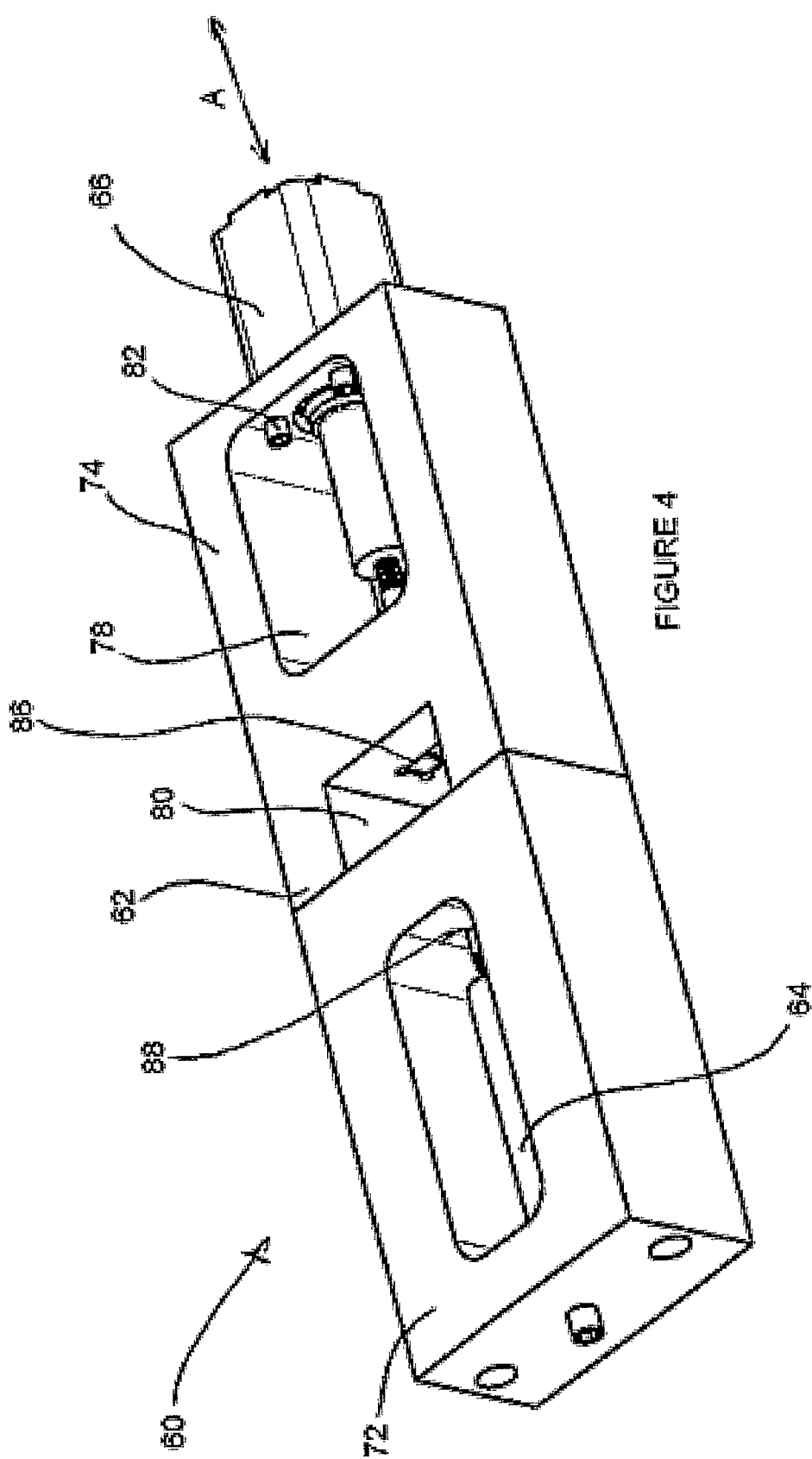
FIG. 4 is an isometric view of the reagent dispensing apparatus according to the present invention.

In FIG. 4 a reagent dispense apparatus 60 is shown having a housing 62, a first linear actuator in the form of a Piezo stack 64 and a second linear actuator in the form of a stepper motor 66.

Figure 5:
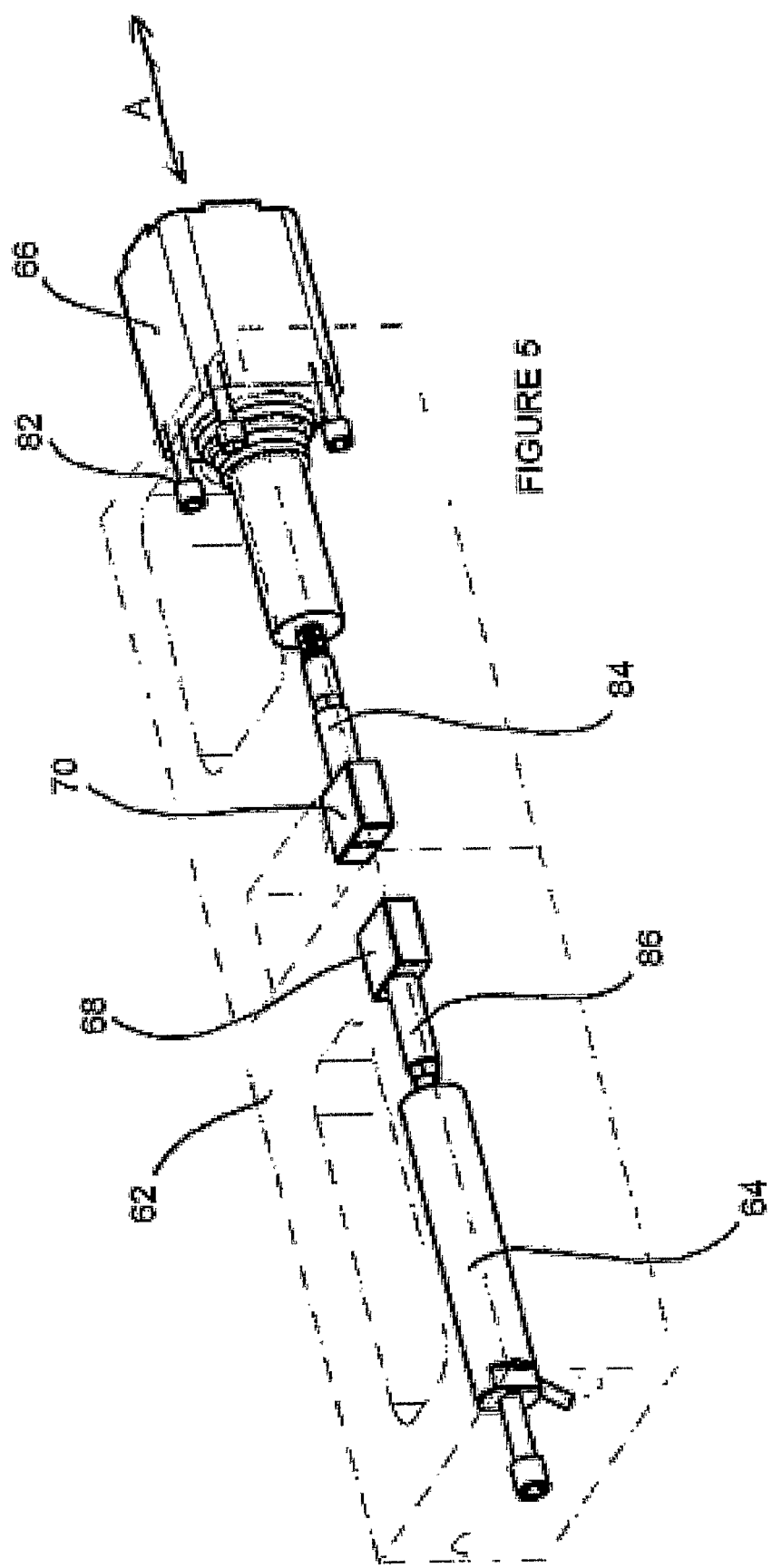
FIG. 5 is an isometric view of the reagent dispensing apparatus of FIG. 4 with the housing shown in dashed lines.

Turning now to FIG. 5, the Piezo stack 64 drives a hammer 68 and the stepper motor 66 positions an anvil 70. Referring once again to FIG. 4, the housing 62 is made up of a hammer body 72 and an anvil body 74. The hammer body 72 defines a Piezo aperture 76 and the anvil body 74 defines a stepper motor aperture 78. The anvil body 74 also defines a shroud receiving recess 80.

The stepper motor 66 is fixed to the anvil body 74 by a series of bolts 82. The stepper motor extends longitudinally through the stepper motor aperture 78 and moves the anvil 70 in a plane indicated at A in FIGS. 4 and 5. The step motor actuates the anvil 70 by way of an actuation rod 84. The anvil 70 is slidably retained within an anvil aperture 86 as shown in FIG. 4.

The Piezo stack 64 actuates the hammer 68 in the plane A as indicated in FIGS. 4 and 5 by way of an actuation rod 86. The actuation rod acts in a Piezo aperture 88 as shown in FIG. 4.

Figure 6:
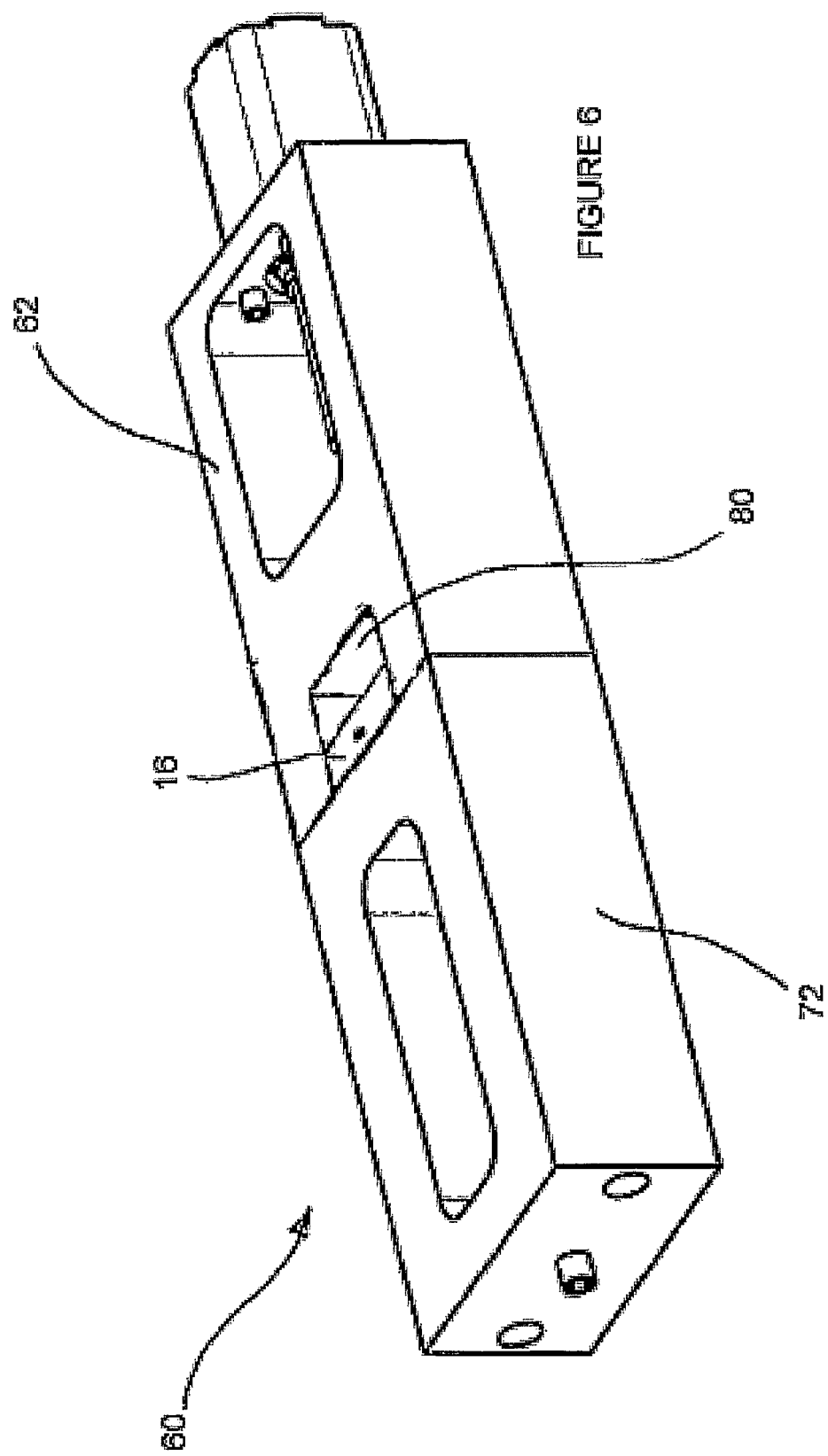
FIG. 6 is an isometric view of the reagent dispensing apparatus of FIG. 4, and the shroud of the dispense device of FIG. 1.

In FIG. 6, the reagent dispense apparatus 60 is shown having received the dispense cartridge 10, the cartridge body 14 of which is not shown for clarity. The shroud portion 16 of the cartridge 10 is shown within the shroud receiving recess 80 in a position in which it abuts an inwardly facing surface of the hammer body 72. The relative positions of the shroud portion 16, the hammer 68 and the anvil 70 are shown in FIG. 7.

Figure 7:
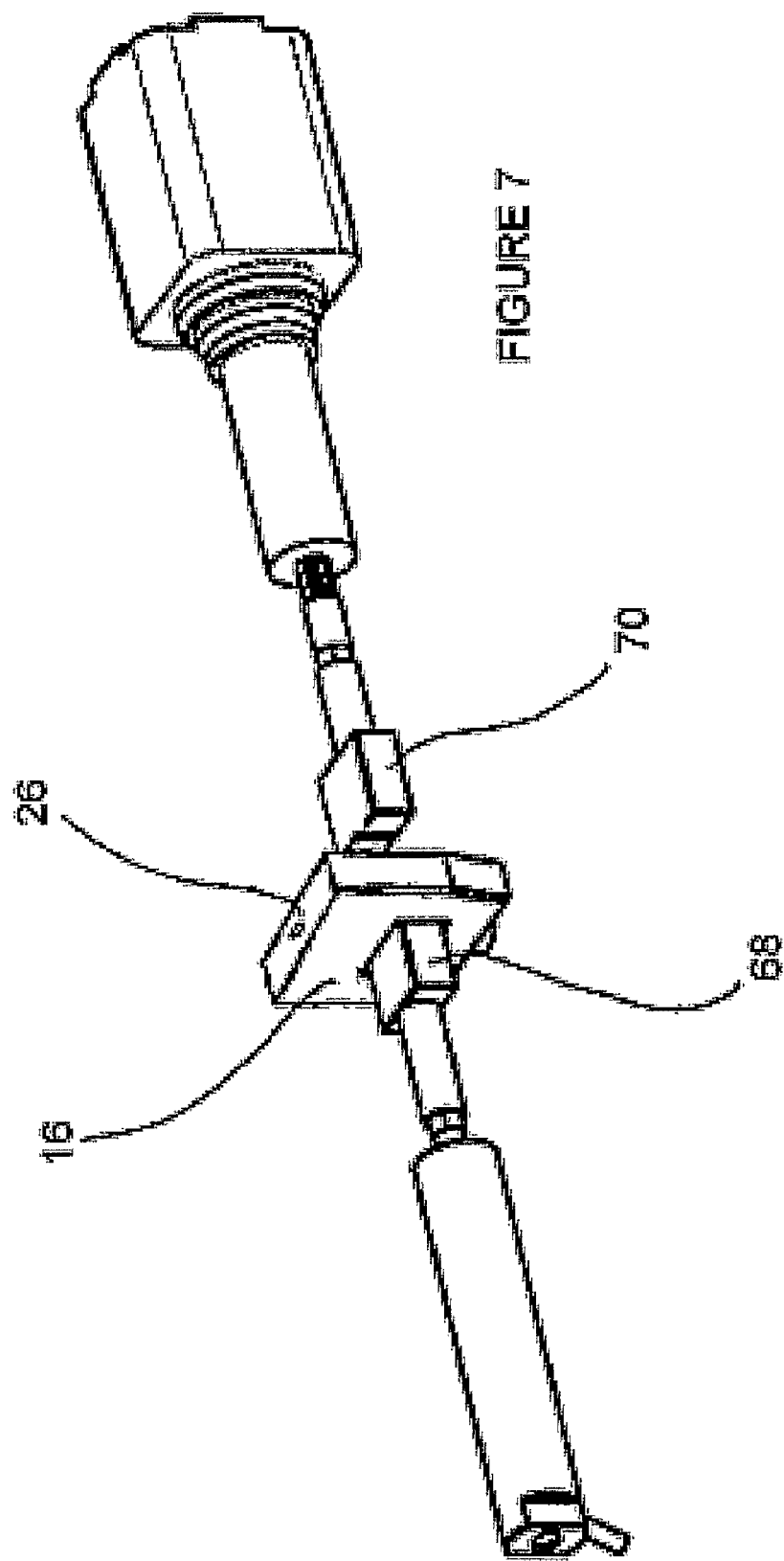
FIG. 7 is an isometric view of the. reagent dispensing apparatus of FIG. 4, with the housing removed and including the shroud of the reagent dispense device of FIG. 1.

In FIG. 7, the hammer 68 is shown in its actuated position. In this position, the extreme end of the hammer 68 extends beyond the inwardly facing surface of the hammer body 72 and extends into the aperture 24 of the shroud portion 16. The anvil 70 is shown in its retracted position in which it is remote from the shroud portion 16.

In use, the reagent dispensing apparatus 60 forms part of a reagent dispensing machine which is not shown for clarity. The reagent dispensing machine might include multiple reagent dispense apparatus 60. The machine would also include a carousel containing multiple reagent dispense cartridges 10. The required reagent dispense cartridge 10 is brought on station at the reagent dispense apparatus and its shroud 16 is inserted into the recess 80 as shown in FIGS. 6 and 7. This brings the dispensing tube 26 into contact the hammer 68 as shown in hidden detail in FIG. 8.

With reference now to FIG. 8, having received the shroud portion 16, the stepper motor 66 is then controlled by a controller 90 to drive the anvil 70 in direction B as shown in FIG. 8. The controller 90 drives the anvil 70 towards the hammer 68 until it detects a voltage generated in the Piezo stack 64 as a result of the anvil 70 contacting the hammer 68. The controller then stops and reverses the stepper motor 66 driving the hammer 70 in direction C a pre-determined distance as shown in FIG. 8. The position of the anvil 70 is thereby calibrated to an operation position in order to deliver the required stroke in the actuator to dispense a volume of fluid from the dispensing tube 26. With the anvil position calibrated, the controller 90 controls the Piezo stack 64 to drive the hammer 68 between its actuated position as shown in FIG. 8 and a retracted position. In order to dispense the required volume of reagent, the controller drives the Piezo stack 64 to cycle the hammer in order to strike the dispensing tube 26 the required number of times for the required volume of reagent to be dispensed.

Returning now to FIG. 2, as reagent is dispensed from the dispensing tube 26, it follows that the level of reagent 30 will fall. However, since the gas space 46 is an enclosed gas space it follows that in order for reagent to continue to be dispensed from the reservoir 32, the volume of the gas space above the reagent 28 will need to increase accordingly. This increased volume of gas is drawn from atmosphere and through the liquid via the vents 40.

The volume of reagent in the reservoir 32 reduces with each successive strike of the hammer 68. Consequently, the sub-atmospheric pressure observed in the gas space 46 will decrease with successive dispenses until such time as the pressure observed at the vent outlet has fallen sufficiently to allow the separation a bubble from the vent outlet 44. At the moment the bubble separates from the vent outlet 44, the pressure in the head space 46 rises to a level slightly above the level before the formation of a bubble. The bubble passes up through the reagent 28 into the head space 46. The process then begins afresh, with the pressure in the head space 46 gradually decreasing to the point where a bubble is generated and released at which point the pressure in the gas space rises once again. This cycling of decreased sub-atmospheric pressure followed by bubble release causes an oscillation in the head pressure and therefore in the reservoir pressure.

It has been observed that the size of the bubble generated at the outlet 44 is proportional to the volume of gas above the reagent 28. Since it is desired to minimise the magnitude of the reservoir pressure oscillation, it is advantageous to reduce the size of the bubble by reducing the volume of gas above the reagent.

Figure 10:
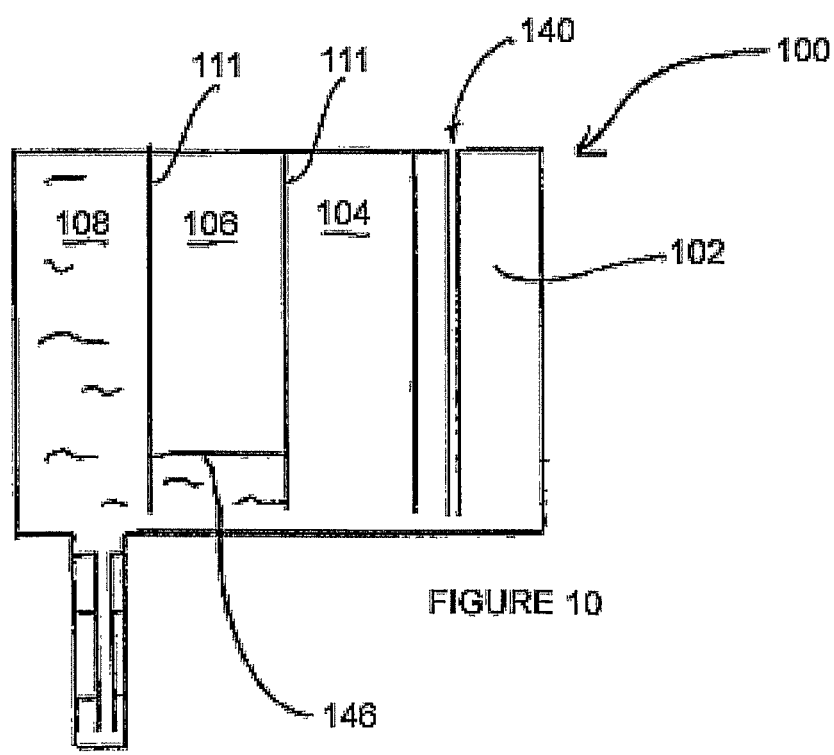
FIG. 10 is a sectioned side view of the reagent dispense device of FIG. 9 showing the third chamber part-full.

Referring now to FIGS. 9, 10 and 11, a cartridge 100 is provided having a vent 140, similar to the vent 40 of the cartridge 10. However, in contrast to the cartridge 10, cartridge 100 is provided with 4 reagent chambers 102, 104, 106, 108 connected by a series of apertures 109 defined by chamber dividers 111. In FIG. 9, the reagent level 130 is shown half way down the first chamber 102. Consequently, the effective head space 146 is only half the volume of the first chamber 102.

Referring now to FIG. 10, more reagent has now been dispensed from the cartridge 100 and the reagent level now is approximately three quarters of the way down the third chamber 106, with the first and second chambers 102, 104 being empty. It will be appreciated therefore at the maximum effective gas space is equal to the volume of one of the chambers 102, 104, 106, 108. Therefore, for virtually no loss in the volume of the reagent which can be contained by the cartridge 100, the maximum effective gas space of the cartridge is equal to one quarter of the reagent volume of the cartridge.

It will be appreciated that whilst the embodiment describes in FIGS. 9, 10 and 11 has 4 chambers, a cartridge with any number of chambers could readily be provided in order to further reduce the effective head space of the cartridge.

In addition to the effect on bubble size of the volume of the gas space above the reagent, it has been observed that providing a vent of decreased diameter decreases the size of the bubbles. However, a large decrease in vent diameter results in an increase in the negative pressure in the gas space required to draw the first bubble from the vent. Once this negative pressure has been established, the production of bubbles causes the pressure to oscillate about that pressure in the manner described above. This means that the sytem takes a period of time to settle before the pressure stabilises about a mean.

Providing a vent with a larger diameter allows the first bubble to be drawn at a lower negative pressure, but the magnitude of the resulting pressure oscillations is greater since a larger volume of gas must be pulled to produce a bubble. The design of the vent must therefore be optimised for each application of the cartridge, dependent on, for example, the viscosity or surface tension of the fluid and the frequency of dispensing.

It is conceivable within the scope of the invention that the Piezo stack 64 could be replaced with a different form of fast acting reciprocating linear drive. Similarly, the stepper motor 66 could readily be replaced with a similar form of drive.

Furthermore, the invention is not limited to the particular size or shape of cartridge disclosed herein.

The accuracy of dispense of the device described above is dependent upon the accurate control of the stroke of the Piezo stack. In this way the extent of compression of the dispense tube is configured to give the required dispensed volume of fluid.

However, frequently the volume of fluid dispensed is hypercritical to the accuracy of the test. Accordingly it is advantageous to provide a secondary measurement device to validate the length of stroke of the Piezo stack to the dispensed volume.

In FIG. 12, the reagent dispensing system of FIG. 8 is shown with the addition of a droplet size measurement device 92 which is arranged to measure the size (and thereby the volume) of droplet 94 after it has been dispensed from the tube 26. The measurement device interrogates the droplet optically in a known manner in order to deduce the volume of the droplet. If the droplet size is smaller than the volume required for the particular IV test, then the controller 90 alters the stroke of the Piezo stack in order to compress the tube 26 by the required volume to deliver the correct volume of reagent. Alternatively, if the total volume to be dispensed is made up of a number of individual droplets, then the total number of strikes of the tube 26 may be altered by the controller 92 in order to deliver the correct volume of reagent.

In an alternative embodiment, the measurement device 92 is replaced by scales which are placed under the cuvette in order to accurately weigh the volume of reagent fluid dispensed. These scales provide a signal to the controller in order that the stroke of the Piezo stack or number of strikes may be altered as described above.

In a yet further embodiment, a micro flow meter is placed within the cartridge, preferably at a position just upstream of the pipe inlet. The Piezo stroke is then controlled by the controller by way of feedback from the flow meter.

FIG. 13 shows the shroud portion 16 of the device shown in FIG. 1 and described in detail above.

FIG. 14 shows an alternative embodiment of shroud portion 16' which defines an aperture 24' in the rear face 22' for receiving the hammer. The front face 20' does not define an aperture and but is rather a solid body of material which forms an integral anvil.

In FIG. 15 a further alternative embodiment of shroud portion 16" is shown having a front face 20" similar to that shown in FIG. 14. The rear face 22" is also similar to that shown in FIG. 14 with the addition of an actuation block 21 which is held in place by an adhesive film which is arranged on the rear face 22" (not shown for clarity). This actuation block is actuated by the hammer to strike the pipe 24. The shroud portion 16" is also provided with a cap 23 to prevent evaporation of the reagent from the end of the pipe 24. The cap also serves the purpose of maintaining a humid environment in the region of the end of the pipe 24 so as to maintain the fluid meniscus to ensure reliable dispense. It will be appreciated that the cap 23 could equally be applied to any of the other shroud embodiments without departing from the scope of the invention.

In addition or in the alternative to the cap, a valve, for example a zero displacement valve, may be positioned at the upper end of the pipe 24 to prevent leakage of reagent from the pipe during handling.

Lastly, whilst the cartridge is described with reference to a reagent fluid, it is conceivable within the scope of the invention that the cartridge is suitable for dispensing a range of liquids, and is particularly suited for dispensing small volumes of liquid which require very accurate dispense. The description of the invention with respect to reagent dispense is therefore not intended to limit the scope of the invention to the dispense of reagents, but rather to provide an example of a form of liquid which could readily be dispensed by the invention.

For example fluids might be medicines, medicaments, medical preparations such as cough mixtures, liquid drugs, enzymes, lipids, blood or blood components, urine or plasma.

The invention claimed is:

1. A reagent dispense device comprising,
a reagent reservoir in fluid communication with a deformable dispense tube,
the deformable dispense tube being at least partially compressible, in use, between a hammer and an anvil, so as to dispense a volume of reagent from the tube,
wherein, in use, the reservoir defines an enclosed gas space above the reagent, and the device including a gas vent for, in use, admitting gas to the gas space in response to a dispense of reagent from the tube,
the passage of gas into the gas space serving to control the reservoir pressure as the reservoir is depleted by subsequent dispensing of reagent;
wherein the reservoir defines multiple chambers which are successively drained of reagent so as to minimize the effective above the reagent.

2. The device of claim 1 wherein the vent has an outlet arranged adjacent a base of the reservoir.

3. The device of claim 2 wherein the outlet defines at least in part a saw tooth configuration in order to minimise surface tension effects at the outlet.

4. The device of claim 2 wherein the outlet is arranged at an angle to an elongate axis of the vent to as to provide an elliptical outlet.

5. The device of claim 1 wherein the vent has an inlet arranged at a top surface of the reservoir.

6. The device of claim 1 wherein the vent is in the form of a tube.

7. The device of claim 1 wherein the chambers are separated by a series of upstanding walls which extend from an upper wall of the reservoir to a position adjacent a base of the reservoir.

8. The device of claim 7 wherein the upstanding walls define a series of conduits between the compartments, each of the conduits being arranged adjacent the reservoir base.

9. The device of claim wherein the device includes a shroud which partially surrounds the dispense tube so as to protect the tube from damage.

10. The device of claim 9 wherein the shroud has a portion adjacent to, but not touching, an outlet of the tube, 11. The device of claim 9 wherein the shroud defines an aperture shaped to accept the anvil in order to allow the anvil access to the tube in order to dispense the reagent.

12. The device of claim 1 wherein the device is provided with a radio frequency identification (RFID) chip containing data including one or more of reagent type, shelf life, date of manufacture, remaining reagent volume, and other such information as may be required.

* * * * *